United States Patent
Simonnet et al.

(10) Patent No.: US 9,636,297 B2
(45) Date of Patent: May 2, 2017

(54) EXTEMPORANEOUS CARE PRODUCT BASED ON A LYOPHILIZATE OF MICROORGANISMS AND SURFACTANT(S) WITH AN HLB GREATER THAN OR EQUAL TO 12

(75) Inventors: Jean-Thierry Simonnet, Cachan (FR); Karine Lucet-Levannier, Reuil-Malmaison (FR)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 12/990,414

(22) PCT Filed: Apr. 28, 2009

(86) PCT No.: PCT/IB2009/051728
§ 371 (c)(1),
(2), (4) Date: Feb. 8, 2011

(87) PCT Pub. No.: WO2009/133519
PCT Pub. Date: Nov. 5, 2009

(65) Prior Publication Data
US 2011/0150952 A1 Jun. 23, 2011

Related U.S. Application Data

(60) Provisional application No. 61/071,643, filed on May 9, 2008.

(30) Foreign Application Priority Data

Apr. 29, 2008 (FR) ..................................... 08 52889

(51) Int. Cl.
*A61K 8/99* (2006.01)
*A61Q 19/08* (2006.01)
(Continued)

(52) U.S. Cl.
CPC ................ *A61K 8/99* (2013.01); *A61K 8/604* (2013.01); *A61Q 5/12* (2013.01); *A61Q 19/08* (2013.01);
(Continued)

(58) Field of Classification Search
CPC ...... A61K 8/99; A61K 8/604; A61K 2800/84; A61K 2800/88; A61Q 19/08; A61Q 5/12
See application file for complete search history.

(56) References Cited

U.S. PATENT DOCUMENTS 3,615,972 A 10/1971 Morehouse, Jr. et al.
3,939,260 A * 2/1976 Lafon ........................... 424/401
(Continued)

FOREIGN PATENT DOCUMENTS

EP 0 056 219 7/1982
EP 0 315 541 5/1989
(Continued)

OTHER PUBLICATIONS

UNC, The pharmaceutics and Compounding Laboratory, Last Accessed Feb. 1, 2013, Eshelman School of Pharmacy, pp. 1-2.*
(Continued)

*Primary Examiner* — Trevor Love
(74) *Attorney, Agent, or Firm* — Oblon, McClelland, Maier & Neustadt, L.L.P.

(57) ABSTRACT

The present invention relates to a method for the cosmetic treatment of a keratin material comprising at least the steps of: (a) having available a lyophilizate containing at least one live or inactivated, physiologically acceptable microorganism, one of its metabolites or one of its fractions and at least one surfactant with an HLB greater than or equal to 12, (b) having available a physiologically acceptable medium, separate from the said lyophilizate, (c) bringing the said lyophilizate extemporaneously into contact with the said
(Continued)

medium under conditions favorable for the solubilization and/or dispersion of the said lyophilizate in the said medium, and (d) bringing the mixture obtained in the preceding step into contact with the said keratin material. It further relates to a lyophilizate as defined above.

11 Claims, 1 Drawing Sheet

(51) Int. Cl.
*A61K 8/60* (2006.01)
*A61Q 5/12* (2006.01)
(52) U.S. Cl.
CPC ...... *A61K 2800/84* (2013.01); *A61K 2800/88* (2013.01)

(56) References Cited

U.S. PATENT DOCUMENTS

| | | | |
|---|---|---|---|
| 5,412,004 | A | 5/1995 | Tachibana et al. |
| 5,811,487 | A | 9/1998 | Schulz et al. |
| 7,025,955 | B2 * | 4/2006 | Siddiqui et al. ............ 424/70.1 |
| 7,534,443 | B1 | 5/2009 | Azuma et al. |
| 2005/0008666 | A1 * | 1/2005 | Lalaudiere et al. ......... 424/401 |
| 2008/0032384 | A1 | 2/2008 | Nomura |
| 2008/0152738 | A1 | 6/2008 | Azuma et al. |

FOREIGN PATENT DOCUMENTS

| | | |
|---|---|---|
| EP | 1 097 715 | 5/2001 |
| EP | 1 354 593 | 10/2003 |
| EP | 1 741 438 | 1/2007 |
| FR | 2 876 356 | 4/2006 |
| FR | 2 913 337 | 9/2008 |
| JP | 63 96107 | 4/1988 |
| JP | 2 295912 | 12/1990 |
| JP | 6-56680 A | 3/1994 |
| JP | 10-203966 | 8/1998 |
| JP | 10-511110 A | 10/1998 |
| JP | 2004-346073 A | 12/2004 |
| JP | 2005-508220 | 3/2005 |
| JP | 2005-524700 | 8/2005 |
| JP | 2006-509779 | 3/2006 |
| JP | 2008-512485 | 4/2008 |
| JP | 2008-515792 A | 5/2008 |
| WO | 94 02158 | 2/1994 |
| WO | 97 36603 | 10/1997 |
| WO | 98 47374 | 10/1998 |
| WO | 01 45721 | 6/2001 |
| WO | 01 82886 | 11/2001 |
| WO | WO03/040398 * | 5/2003 |
| WO | 2004 024798 | 3/2004 |
| WO | 2006 013420 | 2/2006 |
| WO | WO 2006/040257 A1 | 4/2006 |

OTHER PUBLICATIONS

Dow, Triton BG-10 Surfactant, Accessed Apr. 25, 2014, Dow, pp. 1-2.*

International Search Report issued Mar. 26, 2010 in PCT/IB09/051728 filed Apr. 28, 2009.

Office Action issued Jan. 27, 2015, in Japanese Patent Application No. 2011-506814 (English Translation of Pertinent Part of Office Action).

* cited by examiner

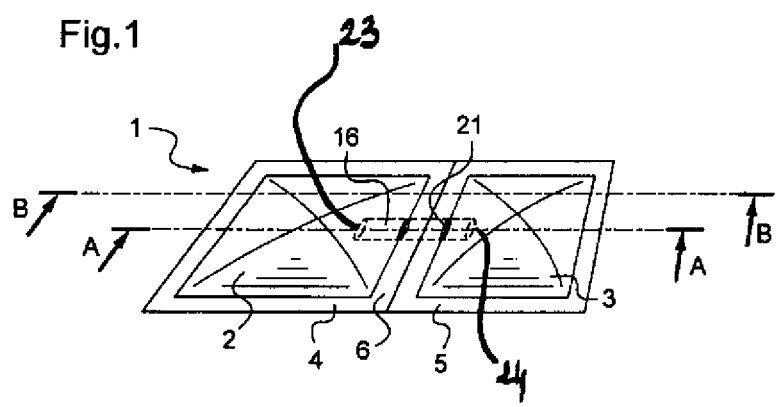
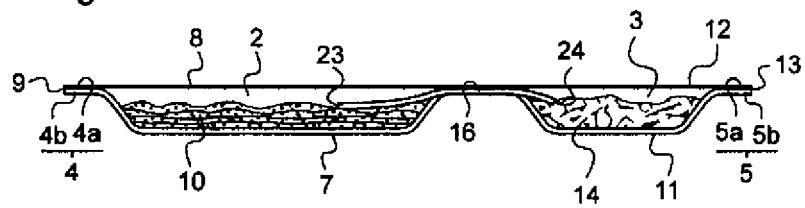
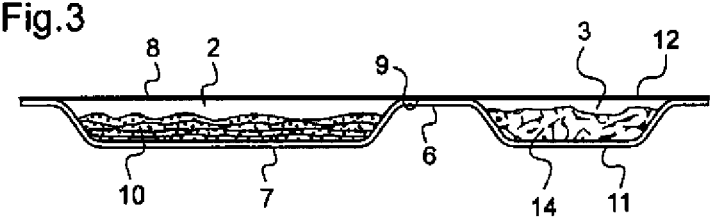

EXTEMPORANEOUS CARE PRODUCT BASED ON A LYOPHILIZATE OF MICROORGANISMS AND SURFACTANT(S) WITH AN HLB GREATER THAN OR EQUAL TO 12

The present invention relates to the field of cosmetic and/or pharmaceutical care of keratin materials, and more particularly the skin.

More particularly, it aims to provide compositions dedicated to the care of keratin materials and using microorganisms.

The incorporation, into galenic formulas, of microorganisms such as thermal plankton or probiotics, either live, or in inactivated form, is particularly advantageous for the dermocosmetic field because of the benefits which they are likely to offer.

Accordingly, the documents WO 01/45721, WO 97/366603 and WO 98/47374 propose using specific bacterial strains for their antifungal and/or bactericidal properties in compositions for cosmetic or pharmaceutical use. Likewise, in the document WO 06/13420, microorganisms, in particular probiotic microorganisms, are more particularly proposed for stimulating the growth of endogenous microorganisms and thereby for protecting the skin against pathogenic microorganisms. In general, the microorganisms are incorporated into the corresponding compositions in live or inactivated form.

However, the introduction of microorganisms, whether in live or inactivated form, into a composition poses problems in particular linked to the biological nature of these active agents.

Accordingly, the introduction of microorganisms in an inactivated form into a composition, for example a cosmetic composition, requires reinforcing the microbiological protection of this composition because they constitute a substrate of choice for the development of yeasts, bacteria and moulds. It is therefore important to combine them with an effective quantity of preservative(s). Now, the presence of preservatives in large quantities in cosmetic products should be avoided for the obvious reason of skin intolerance.

By contrast, the introduction of live microorganisms into galenic compositions requires that the latter are free of preservatives. For obvious reasons, it then becomes very difficult to guarantee the "microbiological cleanliness" of the corresponding composition, under normal conditions of use and over a reasonable timescale which may extend from several weeks to several months.

In addition, it can be understood, in the light of the above observations, why these constraints linked to the biological nature of microorganisms conflict with their use at high concentrations in compositions.

Consequently, the use of microorganisms, live or in inactivated form, in compositions in particular intended for cosmetic or dermatological use poses a problem at the formulation level.

The document JP 63096107 teaches cosmetic products containing one or more microorganisms in lyophilized form, of the bacteria or yeast type.

This type of formulation has the advantages of being easily accessible, of being easy to use and of posing no difficulty and/or constraint in terms of storage. Moreover, it is compatible with the packaging of microorganisms in the state of dormancy.

However, the subsequent formulation of the lyophilizate thus obtained, and in particular its redissolution in an aqueous phase, is not entirely satisfactory.

This problem of redissolution is most particularly exacerbated when the lyophilizate incorporates one or more lyophilization additives as in the case of hydrocolloids such as xanthan gum for example. Being advantageous during lyophilization since they effectively prevent any phenomenon of sedimentation of the microorganism during this operation, they can, on the other hand, be disruptive during subsequent dissolution of the lyophilizate thus obtained. In general, any dissolution occurs with greater difficulty in their presence.

The present invention aims specifically to provide a solution to this problem.

More specifically, the present invention relates, according to a first of its aspects, to a method for the cosmetic treatment of a keratin material comprising at least the steps of:

(a) having available a lyophilizate containing at least one live or inactivated, physiologically acceptable microorganism, one of its metabolites or one of its fractions and at least one surfactant with an HLB greater than or equal to 12, (b) having available a physiologically acceptable medium, separate from the said lyophilizate, (c) bringing the said lyophilizate extemporaneously into contact with the said medium under conditions favourable for the solubilization and/or dispersion of the said lyophilizate in the said medium, and (d) bringing the mixture obtained in the preceding step into contact with the said keratin material.

The inventors have indeed observed that the presence of such a surfactant in the lyophilizate made it possible to significantly facilitate the solubilization and/or dispersion of the said lyophilizate in the physiologically acceptable medium.

This beneficial effect of the said surfactant is particularly advantageous when the lyophilizate contains, in addition to the microorganism considered, a lyophilization additive.

Accordingly, according to a particular embodiment of the invention, the lyophilizate according to the invention further contains at least one lyophilization additive, chosen in particular from silica and its derivatives, clays, cellulose derivatives (HEC, HPC, HMPC and the like), polymers of natural origin such as alginates, xanthans, carob gum, guar gums, pectins, agar, carrageenans, polymers of bacterial origin such as hyaluronic acid, dextran, gellan and hydrogels such as carbomers, derivatives of AMPS.

This is advantageously a polymer of natural origin such as for example a xanthan.

According to one variant embodiment, steps (c) and (d) are consecutive.

According to another variant embodiment, steps (c) and (d) are carried out simultaneously. In other words, the mixing of the lyophilizate and the physiologically acceptable medium is carried out in the presence of, or even in contact with, the said keratin material.

According to a preferred variant embodiment, the lyophilizate exists in a dry galenic form, for example of the tablet or oral lyophilizate type, and the associated physiologically acceptable medium is provided in fluid form favourable for the solubilization and/or dispersion of the lyophilizate.

According to another of its aspects, the present invention relates to a lyophilizate containing at least one live or inactivated physiologically acceptable microorganism, one of its metabolites or one of its fractions and at least one surfactant with an HLB greater than or equal to 12.

According to a preferred variant embodiment, this lyophilizate further contains at least one lyophilization additive such as for example silica and its derivatives, clays, cellulose derivatives (HEC, HPC, HMPC and the like), polymers of natural origin such as alginates, xanthans, carob gum, guar gums, pectins, agar, carrageenans, polymers of bacterial origin such as hyaluronic acid, dextran, gellan and hydrogels such as carbomers, derivatives of AMPS.

More particularly, this is a polymer of natural origin, and in particular a xanthan.

According to yet another of its aspects, the present invention relates to an extemporaneous cosmetic or dermatological care product for a keratin material comprising at least:
  i. a first composition completely or partially formed of a lyophilizate containing at least one live or inactivated physiologically acceptable microorganism, one of its metabolites or one of its fractions and at least one surfactant with an HLB greater than or equal to 12, and
  ii. a second composition containing a physiologically acceptable medium separate from the said lyophilizate, the said medium being capable of solubilizing or dispersing the said lyophilizate.

In particular, the second composition may be different from water.

Such a product may advantageously combine the two compositions separately, in a single packaging.

More particularly, the first composition may be provided in a dry form and the second composition in a fluid, or even liquid, form.

As a variant, the first and second composition may be provided in quantities such that their mixing is intended to provide a single dose for a single use, or so-called travel doses because they are lighter to transport.

Such a product may be designed for skin care or for hair care.

The present invention is further intended to provide a packaging set comprising at least:
  i. a first compartment containing at least one lyophilizate containing at least one live or inactivated physiologically acceptable microorganism, one of its metabolites or one of its fractions and at least one surfactant with an HLB greater than or equal to 12,
  ii. a second compartment containing a physiologically acceptable medium separate from the said lyophilizate, the said second compartment being, prior to the use of the set, isolated in a leakproof manner from the first compartment, and
  iii. means for, in response to actuation, allowing communication to be established between the first and second compartments, and the said lyophilizate to be brought into contact with the said physiologically acceptable medium.

Advantageously, such a set may further comprise a means appropriate for the distribution of the lyophilizate and of the physiologically acceptable medium.

According to one variant embodiment, the physiologically acceptable medium, when it is in the liquid state, may be used to impregnate a substrate for application, in particular inside the second compartment, for example a fibrous substrate or a substrate of the sponge or wipe type. This substrate for application is then placed directly in the compartment dedicated for the physiologically acceptable medium.

For example, such substrates may be impregnated with an aqueous composition such as a makeup-removing lotion, a makeup-removing milk or a care agent for example, and, they are, after bringing into contact with the said lyophilizate, applied directly to the face, the body or the hair.

These substrates may also be impregnated with an anhydrous composition containing, for example, a mixture of oils and surfactants.

The methods, products and sets according to the invention are found to be particularly advantageous since, on the one hand, they are compatible with the use of microorganisms, whether they are live or inactivated, and, on the other hand, they make it possible to effectively prevent, over a long period of time, any risk of microbiological or bacteriological contamination without requiring the use of preservatives or of excessive quantities of preservatives.

These methods, products and sets according to the invention are thus further found to be advantageously appropriate for the use of large quantities of microorganisms.

These methods, products and sets according to the invention are also found to be particularly advantageous in that they make it possible to facilitate the solubilization and/or dispersion of the lyophilizate in the physiologically acceptable medium, in particular when the lyophilized solution contains at least one auxiliary compound of the lyophilization additive type in particular as described above, or even a gelling agent and/or a thickener.

Microorganisms

The microorganisms suitable for the invention are physiologically acceptable. In other words, they are microorganisms which may be administered with no risk to animals or humans.

In particular, it is possible to use in the present invention at least one microorganism chosen from so-called probiotic type microorganisms, nonphotosynthetic filamentous bacteria, one of the extracts thereof and one of the mixtures thereof.

According to one variant of the invention, this microorganism is used in isolated form, that is to say not mixed with one or more compounds liable to be combined with it in its natural environment or its original culture medium.

For the purposes of the invention, the term metabolite denotes any substance derived from the metabolism of the microorganisms considered according to the invention and also having an efficacy comparable to that of the native microorganism.

For the purposes of the invention, the term fraction denotes more particularly a fragment of the said microorganism having an efficacy comparable to that of the native microorganism.

This term extends in particular to the extracts of microorganisms, and in particular nonphotosynthetic filamentous bacteria, in particular as defined more precisely below.

Probiotic Microorganisms

For the purposes of the present invention, the expression "probiotic microorganism" is understood to mean a live microorganism which, when consumed in adequate amounts, has a positive effect on the health of its host "Joint FAO/WHO Expert Consultation on Evaluation of Health and Nutritional Properties of Probiotic in Food Including Powder Milk with Live Lactic Acid Bacteria, 6 Oct. 2001", and which can in particular improve the intestinal microbial balance.

The probiotic microorganisms suitable for the invention may be chosen in particular from ascomycetes such as *Saccharomyces, Yarrowia, Kluyveromyces, Torulaspora, Schizosaccharomyces pombe, Debaromyces, Candida, Pichia, Aspergillus* and *Penicillium*, bacteria of the genus *Bifidobacterium, Bacteroides, Fusobacterium, Melissococcus, Propionibacterium, Enterococcus, Lactococcus, Staphylococcus, Peptostrepococcus, Bacillus, Pediococcus,*

*Micrococcus, Leuconostoc, Weissella, Aerococcus, Oenococcus, Lactobacillus* and mixtures thereof.

As ascomycetes which are particularly suitable for the present invention, there may be mentioned in particular *Yarrowia lipolitica* and *Kluyveromyces lactis*, as well as *Saccharomyces cereviseae, Torulaspora, Schizosaccharamyces pombe, Candida* and *Pichia*.

As regards the probiotic microorganisms, these are the following bacteria and yeast genera which are generally used:

lactic acid bacteria: which produce lactic acid by fermentation of sugar. Depending on their morphology, they are divided into two groups:

*Lactobacillus* species: *Lactobacillus acidophilus; amylovorus, casei, rhamnosus, brevis, crispatus, delbrueckii* (subsp *bulgaricus, lactis*), *fermentum, helveticus, gallinarum, gasseri johnsonii, paracasei, plantarum, reuteri, salivarius, alimentarius, curvatus, casei* subsp. *casei, sake,*

Gocci: *Enterococcus* (*faecalis, faecium*), *Lactococcus lactis* (subspp *lactis* or *cremoris*), *Leuconstoc mesenteroides* subsp *dextranicum, Pediococcus acidilactici, Sporolactobacillus inulinus, Streptococcus salvarius* subsp. *Thermophilus, Streptococcus thermophilus, Staphylocccus carnosus, Staphylococcus xylosus,* bifidobacteria or *Bifidobacterium* species: *Bifidobacterium adolescentis, animalis, bifidum, breve, lactis, longum, infantis, pseudocatenulatum* yeasts: *Saccharomyces* (*cerevisiae* or alternatively *boulardii*), other sporulated bacteria: *Bacillus* (*cereus* var *toyo* or *subtilis*), *Bacillus coagulans, Bacillus licheniformis, Escherichia coli* strain nissle, *Propionibacterium freudenreichii,* and mixtures thereof.

The lactic acid bacteria and the bifidobacteria are the probiotics most often used.

Specific examples of probiotic microorganisms are *Bifidobacterium adolescentis, Bifidobacterium animalis, Bifidobacterium bifidum, Bifidobacterium breve, Bifidobacterium lactis, Bifidobacterium longum, Bifidobacterium infantis, Bifidobacterium pseudocatenulatum, Lactobacillus acidophilus* (NCFB 1748); *Lactobacillus amylovorus, Lactobacillus casei* (Shirota), *Lactobacillus rhamnosus* (strain GG), *Lactobacillus brevis, Lactobacillus crispatus, Lactobacillus delbrueckii* (subsp *bulgaricus, lactis*), *Lactobacillus fermentum, Lactobacillus helveticus, Lactobacillus gallinarum, Lactobacillus gasseri, Lactobacillus johnsonii* (CNCM 1-1225), *Lactobacillus paracasei, Lactobacillus plantarum, Lactobacillus reuteri, Lactobacillus salivarius, Lactobacillus alimentarius, Lactobacillus curvatus, Lactobacillus casei* subsp. *casei, Lactobacillus sake Lactococcus lactis, Enterococcus* (*faecalis, faecium*), *Lactococcus lactis* (subspp *lactis* or *cremoris*), *Leuconstoc mesenteroides* subsp *dextranicum, Pediococcus acidilactici, Sporolactobacillus inulinus, Streptococcus salvarius* subsp. *Thermophilus, Streptococcus thermophilus, Staphylocccus carnosus, Staphylococcus xylosus, Saccharomyces* (*cerevisiae* or alternatively *boulardii*), *Bacillus* (*cereus* var *toyo* or *subtilis*), *Bacillus coagulans, Bacillus licheniformis, Escherichia coli* strain nissle, *Propionibacterium freudenreichii* and mixtures thereof.

More particularly, it may be at least one probiotic microorganism derived from the group of lactic acid bacteria, such as in partiuclar *Lactobacillus* and/or *Bifidobacterium*. By way of illustration of these lactic acid bacteria, mention may more particularly be made of *Lactobacillus johnsonii, Lactobacillus reuteri, Lactobacillus rhamnosus, Lactobacillus paracasei, Lactobacillus casei* or *Bifidobacterium bifidum, Bifidobacterium breve, Bifidobacterium longum, Bifidobacterium animalis, Bifidobacterium lactis, Bifidobacterium infantis, Bifidobacterium adolescentis* or *Bifidobacterium pseudocatenulatum* and mixtures thereof.

The species that are most particularly suitable are *Lactobacillus johnsonii, Lactobacillus paracasei, Bifidobacterium adolescentis, Bifidobacterium longum* and *Bifidobacterum lactis* NCC 2818 which were respectively deposited according to the Budapest Treaty with Institut Pasteur (28 rue du Docteur Roux, F-75024 Paris cedex 15) on Jun. 30, 1992, Jan. 1, 1999, Apr. 15, 1999, Apr. 15, 1999, Jun. 7, 2005 under the following names CNCM I-1225, CNCM I-2116, CNCM I-2168 and CNCM I-2170 and CNCM I-3446, and the genus *Bifidobacterium longum* (*BB*536) and mixtures thereof.

Nonphotosynthetic Filamentous Bacterium

By way of illustration of nonphotosynthetic filamentous bacteria, there may be mentioned in particular the bacterial extracts prepared from nonphotosynthetic filamentous bacteria as defined according to the classification of Bergey's Manual of Systematic Bacteriology (vol. 3, sections 22 and 23, 9th edition, 1989), among which there may be mentioned the bacteria belonging to the order Beggiatoales, and more particularly the bacteria belonging to the genera *Beggiatoa, Vitreoscilla, Flexithrix* or *Leucothrix*.

The bacteria which have just been defined and several of which have already been described generally have an aquatic habitat and may be found in particular in marine waters or in thermal waters.

They may be in particular at least one of the nonphotosynthetic filamentous bacteria or one of their extracts, for example chosen from:

*Vitreoscilla filiformis* (ATCC 15551)
*Vitreoscilla beggiatoides* (ATCC 43181)
*Beggiatoa alba* (ATCC 33555)
*Flexithrix dorotheae* (ATCC 23163)
*Leucothrix mucor* (ATCC 25107)
*Sphaerotilus natans* (ATCC 13338).

The expression "bacterial extract" according to the invention is understood to mean an extract of the bacterial biomass or any active fraction of the said extract, in particular:

(i) bacterial cells isolated from the culture medium, which have been concentrated, for example by centrifugation ("nonstabilized cellular extract"); or (ii) bacterial cells that have been concentrated (i), and then subjected to an operation for breaking the envelopes of the bacterial cells by any means known to a person skilled in the art, such as the action of ultrasound or preferably autoclaving ("stabilized cellular extract"). The expression "envelopes" is understood to mean the bacterial wall and optionally the subjacent membranes;

(iii) the supernatant obtained by filtration of the stabilized cellular extract (ii), or any active fraction of the said extract.

These extracts or fractions may be preserved for example by freezing the said extracts or the said fractions and used after thawing.

The extract of nonphotosynthetic filamentous bacteria which can be used according to the invention is preferably chosen from a cellular extract, the supernatant of the said cellular extract or an active fraction of the said cellular extract.

Preferably, the extract of nonphotosynthetic filamentous bacteria is a cellular extract of *Vitreoscilla filiformis*.

Preferably, an extract of *Vitreoscilla filiformis* (ATCC 15551) will be used.

To prepare the bacterial extract according to the invention, it is possible to culture the said bacteria according to methods known to a person skilled in the art, or to refer in particular to the description of Patent Application WO-A-94-02158. A cellular extract is obtained whose supernatant may be separated for example by filtration and centrifugation. The extract may be used in aqueous form or in lyophilized form.

These bacteria are advantageously present in the lyophilizate. However, it is also possible to envisage their being present in the galenic form containing the lyophilizate.

It is generally possible to use from 0.001 to 10% by weight, and in particular from 0.005 to 5% by weight, of dry extract of nonphotosynthetic filamentous bacteria relative to the total weight of the galenic form intended to form the whole or part of the lyophilizate.

Use is preferably made of a quantity ranging from 0.01 to 3% by weight of dry extract of nonphotosynthetic filamentous bacteria relative to the total weight of the galenic form intended to form the whole or part of the lyophilizate.

This microorganism or these microorganisms may be further combined with at least one live microorganism of the skin flora.

By way of illustration of this type of microorganisms, there may be mentioned in particular:

*staphylococcus epidermis, S. haemolyticus, S. homonis, S. similans*, also chosen or not chosen from these microorganisms,

*corynobacterium lipophiles, C. jeikeium, C. urealyticum, C. minutissimum*,

*Propionobacter granulosum, P. avidum*,

Micrococcus luteus, M varians

*Streptococcus A, C and G and*

*Brevibacterium*

These microorganisms are advantageously present in the lyophilizate. However, it is also possible to envisage their being present in the galenic form containing the lyophilizate.

In the compositions according to the invention, use will be generally made of $10^2$ to $10^{15}$ cfu/g of live microorganism(s) of the skin flora relative to the total weight of the galenic form wholly or partly formed of the lyophilizate.

The lyophilizate may contain from $10^1$ cfu/g to $10^{15}$ cfu/g, for example from $10^1$ cfu/g to $10^{12}$ cfu/g of microorganism(s).

The microorganisms and/or fractions and/or metabolites thereof may be formulated in a quantity equivalent to at least $10^1$ cfu/g, in particular at doses varying from $10^1$ to $10^{15}$ cfu/g, and more particularly from $10^3$ to $10^{12}$ cfu/g of the lyophilized formula or support containing them.

The fractions and/or metabolites of the microorganisms may be formulated in a quantity equivalent to at least 0.1% of active material or dry matter and up to 50%, and more particularly from 1% to 40% of active material or dry matter, of the lyophilized formula or support containing them.

As specified above, the microorganisms may be used according to the invention in live or inactivated form with the exception of nonphotosynthetic filamentous bacteria such as *Vitreoscilla filiformis*, used in the form of an extract.

For the purposes of the present invention, a live form of a microorganism is intended to cover a form having the capacity to multiply provided it is placed in an environment favourable to the recovery of this capacity. Accordingly, for the purposes of the present invention, the term live covers the so-called state of "dormancy" in which the microorganisms may be placed following a physicochemical treatment such as for example lyophilization.

For the purposes of the present invention, the term inactivated denotes, for its part, microorganisms which have been subjected to a treatment intended to kill them. Such treatments may consist, by way of nonlimiting example, of a treatment in an autoclave, by ultrasound, high-pressure homogenization or osmotic shock.

The inactivated microorganisms for the purposes of the invention may be either intact or in fractionated form. This may for example be an extract of a microorganism or alternatively a lysate of a microorganism. The preparation of these lysates and/or extracts are within the competence of persons skilled in the art.

The microorganism(s), metabolite(s) or fraction(s) is (are) used in a lyophilized form further comprising at least one surfactant with an HLB greater than or equal to 12.

Surfactants with an HLB Greater than or Equal to 12

The surfactants suitable for the invention have an HLB greater than or equal to 12, in particular greater than or equal to 14, preferably greater than or equal to 16.

The expression "HLB greater than or equal to 12 (respectively 14, 16)" is understood to mean a surfactant having, at 25° C., an HLB (hydrophilic-lipophilic balance) within the meaning of GRIFFIN greater than or equal to 12 (respectively 14, 16).

The HLB value according to GRIFFIN is defined in J. Soc. Cosm. Chem. 1954 (volume 5), pages 249-256.

Reference may also be made to the document "Encyclopedia of Chemical Technology, KIRK-OTHMER", volume 22, p. 333-432, 3rd edition, 1979, WILEY, for the definition of the properties and functions (emulsifier) of surfactants, in particular p. 347-377 of this reference, for nonionic surfactants.

The surfactant with an HLB greater than or equal to 12 may be ionic, nonionic or of a mixed ionic and nonionic nature.

Use may be made in particular of the surfactants with an HLB greater than or equal to 12 which are cited in McCutcheons Emulsifiers & Detergents, International Edition of 1998 and later. By way of examples, mention may be made of those given on pages 223 to 231 of the section HLB Index of the 1998 edition.

Nonionic Surfactants

The nonionic surfactants may be chosen in particular from the alkyl and polyalkyl esters of poly(ethylene oxide), alkyl and polyalkyl ethers of poly(ethylene oxide), alkyl and polyalkyl esters of sorbitan, polyoxyethylenated or not, alkyl and polyalkyl ethers of sorbitan, polyoxyethylenated or not, alkyl and polyalkyl glucosides and polyglucosides, alkyl and polyalkyl esters of sucrose, alkyl and polyalkyl esters of glycerol, polyoxyethylenated or not, alkyl and polyalkyl ethers of glycerol, polyoxyethylenated or not, and mixtures thereof.

1) As alkyl and polyalkyl esters of poly(ethylene oxide), use is preferably made of those having a number of ethylene oxide (EO) units ranging from 2 to 200. Mention may be made for example of stearate 40 EO, stearate 50 EO, stearate 100 EO, laurate 20 EO, laurate 40 EO, distearate 150 EO.

2) As alkyl and polyalkyl ethers of poly(ethylene oxide), use is preferably made of those having a number of ethylene oxide (EO) units ranging from 2 to 200. Mention may be made for example of cetyl ether 23 EO, oleyl ether 50 EO, phytosterol 30 EO, steareth 40, steareth 100, beheneth 100.

3) As alkyl and polyalkyl esters of sorbitan, polyoxyethylenated or not, use is preferably made of those having a number of ethylene oxide (EO) units ranging from 0 to 100. Mention may be made for example of sorbitan laurate 4 or 20 EO, in particular polysorbate 20 (or polyoxyethylene (20) sorbitan monolaurate) such as the product Tween 20 marketed by the company Uniqema, sorbitan palmitate 20 EO, sorbitan 20 EO stearate, sorbitan 20 EO oleate or alternatively Cremophor (RH 40, RH 60 and the like) from BASF.

4) As alkyl and polyalkyl ethers of sorbitan, polyoxyethylenated or not, use is preferably made of those having a number of ethylene oxide (EO) units ranging from 0 to 100.

5) As alkyl and polyalkyl glucosides or polyglucosides, use is preferably made of those containing an alkyl group comprising from 6 to 30 carbon atoms and preferably 6 to 18, or even 8 to 16 carbon atoms, and containing a glucoside group preferably comprising from 1 to 5, in particular 1, 2 to 3 glucoside units. The alkyl polyglucosides may be chosen for example from decyl glucoside ($C_9/C_{11}$ alkyl polyglucoside (1.4)) such as the product marketed under the name Mydol 10® by the company Kao Chemicals or the product marketed under the name Plantacare 2000 UP® by the company Henkel or the product marketed under the name ORAMIX NS 10® by the company SEPPIC; caprylyl/capryl glucoside such as the product marketed under the name Plantacare KE 3711® by the company Cognis or ORAMIX CG 110® by the company SEPPIC; lauryl glucoside such as the product marketed under the name Plantacare 1200 UP® by the company Henkel or Plantaren 1200 N® by the company Henkel; cocoglucoside such as the product marketed under the name Plantacare 818 UP® by the company Henkel; caprylyl glucoside such as the product marketed under the name Plantacare 810 UP® by the company Cognis; and mixtures thereof.

6) As alkyl and polyalkyl esters of sucrose, mention may be made for example of Crodesta F150, sucrose monolaurate marketed under the name Crodesta SL 40, the products marketed by Ryoto Sugar Ester such as for example the sucrose palmitate marketed under the reference Ryoto Sugar Ester P1670, Ryoto Sugar Ester LWA 1695, Ryoto Sugar Ester 01570.

7) As alkyl and polyalkyl esters of glycerol, polyoxyethylenated or not, use is preferably made of those having a number of ethylene oxide (EO) units ranging from 0 to 100 and a number of glycerol units ranging from 1 to 30. Mention may be made for example of hexaglyceryl monolaurate and PEG-30 glyceryl stearate.

8) As alkyl and polyalkyl ethers of glycerol, polyoxyethylenated or not, use is preferably made of those having a number of ethylene oxide (EO) units ranging from 0 to 100 and a number of glycerol units ranging from 1 to 30. By way of example, mention may be made of Nikkol Batyl alcohol 100, Nikkol chimyl alcohol 100.

Anionic Surfactants

The anionic surfactants may be chosen from alkyl ether sulphates, carboxylates, derivatives of amino acids, sulphonates, isethionates, taurates, sulphosuccinates, alkyl sulphoacetates, phosphates and alkyl phosphates, polypeptides and mixtures thereof.

1) As alkyl ether sulphates, mention may be made for example of sodium lauryl ether sulphate (C12-14 70-30) (2.2 EO) marketed under the names SIPON AOS225 or TEXAPON N702 by the company Henkel, ammonium lauryl ether sulphate (C12-14 70-30) (3 EO) marketed under the name SIPON LEA 370 by the company Henkel, ammonium ($C_{12}$-$C_{14}$)alkyl ether (9 EO) sulphate marketed under the name RHODAPEX AB/20 by the company Rhodia Chimie, and the mixture of sodium and magnesium lauryl and oleyl ether sulphate marketed under the name EMPICOL BSD 52 by the company Albright & Wilson.

2) As carboxylates, mention may be made for example of the salts (for example alkali metal salts) of N-acylamino acids, glycol carboxylates, amidoether carboxylates (AEC) and polyoxyethylenated carboxylic acid salts.

The glycol carboxylate type surfactant may be chosen from alkyl glycol carboxylic acids or 2-(2-hydroxyalkyloxy) acetate, salts thereof and mixtures thereof. These alkyl glycol carboxylic acids contain an aliphatic and/or aromatic, saturated or unsaturated, linear or branched alkyl chain having from 8 to 18 carbon atoms. These carboxylic acids may be neutralized with organic or inorganic bases such as potassium hydroxide, sodium hydroxide, triethanolamine, arginine, lysine and N-methylglucamine.

As surfactants of the glycol carboxylic acid type, mention may be made for example of sodium lauryl glycol carboxylate or sodium 2-(2-hydroxyalkyloxy) acetate such as the product marketed under the name Beaulight Shaa® by the company Sanyo, Beaulight LCA-25N® or the corresponding acid form Beaulight Shaa (Acid form)®.

As amidoether carboxylate (AEC), mention may be made for example of sodium lauryl amidoether carboxylate (3 EO), marketed under the name AKYPO FOAM 30® by the company Kao Chemicals.

As polyoxyethylenated carboxylic acid salt, mention may be made for example of oxyethylenated (6 EO) sodium lauryl ether carboxylate ($C_{12-14-16}$ 65/25/10) marketed under the name AKYPO SOFT 45 NV® by the company Kao Chemicals, polyoxyethylenated and carboxymethylated fatty acids of olive oil origin which are marketed under the name OLIVEM 400® by the company BIOLOGIA E TECNOLOGIA, oxyethylenated (6 EO) sodium tridecyl ether carboxylate sold under the name NIKKOL ECTD-6NEX® by the company Nikkol.

3) As derivatives of amino acids, mention may be made in particular of the alkali metal salts of amino acids, such as:
  sarcosinates, such as sodium lauroyl sarcosinate marketed under the name SARKOSYL NL 97® by the company Ciba or marketed under the name ORAMIX L 30® by the company Seppic, sodium myristoyl sarcosinate marketed under the name NIKKOL SARCOSINATE MN® by the company Nikkol, sodium palmitoyl sarcosinate marketed under the name NIKKOL SARCOSINATE PN® by the company Nikkol.
  alaninates, such as N-lauroyl-N-methylamidopropionate marketed by the company SODIUM NIKKOL ALANINATE LN 30® by the company Nikkol, or marketed under the name ALANONE ALE® by the company Kawaken, N-lauroyl-N-methylalanine triethanolamine marketed under the name ALANONE ALTA® by the company Kawaken.
  glutamates, such as triethanolamine monococoylglutamate marketed under the name ACYLGLUTAMATE CT-12® by the company Ajinomoto, triethanolamine lauroylglutamate marketed under the name ACYLGLUTAMATE LT-12® by the company Ajinomoto.
  aspartates, such as the mixture of triethanolamine N-lauroyl-aspartate/triethanolamine N-myristoylaspartate marketed under the name ASPARACK® by the company Mitsubishi.
  glycine derivatives (glycinates), such as sodium N-cocoylglycinate marketed under the names AMILITE GCS-12® and AMILITE GCK 12 by the company Ajinomoto.

citrates such as oxyethylenated (9 moles) citric monoester of coconut alcohols, which is marketed under the name WITCONOL EC 1129 by the company Goldschmidt. galacturonates such as sodium dodecyl-D-galactoside uronate marketed by the company Soliance.

4) As sulphonates, mention may be made for example of alpha-olefin sulphonates such as sodium alpha-olefin sulphonate ($C_{14-16}$) marketed under the name BIO-TERGE AS-40® by the company Stepan, marketed under the names WITCONATE AOS PROTEGE® and SULFRAMINE AOS PH 12® by the company Witco or marketed under the name BIO-TERGE AS-40 CG® by the company Stepan, the secondary sodium olefin sulphonate marketed under the name HOSTAPUR SAS 30® by the company Clariant;

5) As isethionates, mention may be made of acylisethionates such as sodium cocoylisethionate, such as the product marketed under the name JORDAPON CI P® by the company Jordan.

6) As taurates, mention may be made of the sodium salt of palm kernel oil methyltaurate marketed under the name HOSTAPON CT PATE® by the company Clariant; N-acyl N-methyltaurates such as sodium N-cocoyl N-methyltaurate marketed under the name HOSTAPON LT-SF® by the company Clariant or marketed under the name NIKKOL CMT-30-T® by the company Nikkol, sodium palmitoyl methyltaurate marketed under the name NIKKOL PMT® by the company Nikkol.

7) As sulphosuccinates, mention may be made for example of oxyethylenated (3 EO) lauryl alcohol monosulphosuccinate ($C_{12}/C_{14}$ 70/30) marketed under the names SETACIN 103 SPECIAL®, REWOPOL SB-FA 30 K 4® by the company Witco, the disodium salt of a $C_{12}$-$C_{14}$ alcohol hemisulphosuccinate marketed under the name SETACIN F SPECIAL PASTE® by the company Zschimmer Schwarz, oxyethylenated (2 EO) disodium oleamidosulphosuccinate marketed under the name STANDAPOL SH 135® by the company Henkel, oxyethylenated (5 EO) lauryl amide monosulphosuccinate marketed under the name LEBON A-5000® by the company Sanyo, the oxyethylenated (10 EO) disodium salt of lauryl citrate monosulphosuccinate marketed under the name REWOPOL SB CS 50® by the company Witco, ricinoleic monoethanolamide monosulphosuccinate marketed under the name REWODERM S 1333® by the company Witco. It is also possible to use polydimethylsiloxane sulphosuccinates such as disodium PEG-12 dimethicone sulphosuccinate marketed under the name MACKANATE-DC30 by the company MacIntyre.

8) As alkyl sulphoacetate, mention may be made for example of the mixture of sodium lauryl sulphoacetate and disodium lauryl ether sulphosuccinate marketed under the name STEPAN-MILD LSB by the company Stepan.

9) As phosphates and alkylphosphates, mention may be made for example of monoalkyl phosphates and dialkyl phosphates, such as lauryl monophosphate marketed under the name MAP 20® by the company Kao Chemicals, the potassium salt of dodecylphosphoric acid, mixture of mono- and diester (diester predominantly) marketed under the name CRAFOL AP-31® by the company Cognis, the mixture of monoester and diester of octylphosphoric acid, marketed under the name CRAFOL AP-20® by the company Cognis, the mixture of ethoxylated (7 moles of EO) phosphoric acid monoester and diester of 2-butyloctanol, marketed under the name ISOFOL 12 7 EO-PHOSPHATE ESTER® by the company Condea, the potassium or triethanolamine salt of ($C_{12}$-$C_{13}$) monoalkyl phosphate marketed under the references ARLATONE MAP 230K-40® and ARLATONE MAP 230T-60® by the company Uniqema, potassium lauryl phosphate marketed under the name DERMALCARE MAP XC-99/09® by the company Rhodia Chimie, and potassium cetyl phosphate marketed under the name ARLATONE MAP 160K by the company Uniqema.

10) The polypeptides are obtained for example by condensing a fatty chain with the amino acids from cereals and in particular from wheat and oats. As polypeptides, mention may be made of for example the potassium salt of hydrolysed lauroyl wheat protein marketed under the name AMINOFOAM W OR by the company Croda, the ethanolamine salt of hydrolysed cocoyl soybean protein marketed under the name MAY-TEIN SY by the company Maybrook, the sodium salt of oat lauroyl amino acids marketed under the name PROTEOL OAT by the company Seppic, collagen hydrolysate grafted onto copra fatty acid, marketed under the name GELIDERM 3000 by the company Deutsche Gelatine, soybean proteins acylated with hydrogenated copra acids, marketed under the name PROTEOL VS 22 by the company Seppic.

Amphoteric and Zwitterionic Surfactants

The amphoteric and zwitterionic surfactants may be chosen for example from betaines.

As betaines, mention may be made in particular of alkylbetaines such as for example cocobetaine such as the product marketed under the name DEHYTON AB-30® by the company Cognis, laurylbetaine such as the product marketed under the name GENAGEN KB® by the company Clariant, oxyethylenated (10 EO) laurylbetaine, such as the product marketed under the name LAURYLETHER (10 EO) BETAINE® by the company Shin Nihon Rica, oxyethylenated stearylbetaine (10 EO) such as the product marketed under the name STEARYLETHER (10 EO) BETAINE® by the company Shin Nihon Rica.

Most particularly suitable for the invention, as surfactant with an HLB greater than or equal to 12, are the alkyl and polyalkyl esters of poly(ethylene oxide), the alkyl and polyalkyl esters of sorbitan, polyoxyethylenated or not, the alkyl and polyalkyl glucosides or polyglucosides, the alkyl and polyalkyl esters of glycerol, polyoxyethylenated or not, alkyl ether sulphates, sarcosinates and betaines.

The surfactants with an HLB greater than or equal to 12 described above may also be present in combination.

The amount of surfactant with an HLB greater than or equal to 12 in the composition to be lyophilized may vary from 0.1% to 15% by weight, for example from 0.5% to 8% by weight, in particular from 1 to 6% by weight, or even from 2 to 4% by weight relative to the total weight of the said composition.

As for the lyophilizate, it may comprise from 0.5% to 40% by weight, in particular from 0.5% to 25% by weight, in particular from 1% to 18% by weight, for example from 2 to 16% by weight, in particular from 5 to 14% by weight, of surfactant(s) with an HLB greater than or equal to 12, relative to the total weight of the said lyophilizate in the dry state.

The lyophilization may be carried out according to conventional methods.

As regards the principle, lyophilization consists in removing water from a liquid, pasty or solid product, by the combined action of cold and vacuum. When water in the solid state is heated at very low pressure, the water undergoes sublimation, that is to say that it passes directly from the solid state to the gaseous state. The water vapour (or any other solvent) leaves the product and it is captured by freezing with the aid of a condenser, or trapped. This technique makes it possible to preserve both the volume and the appearance of the treated product. It can take place naturally (drying on a mountain), or, more rapidly, in a lyophilizer.

Lyophilization generally comprises three steps: freezing, sublimation and secondary drying.

Freezing consists in bringing a substance very rapidly to a temperature between −20° C. and −80° C., so as to block the water in the form of ice in the situation where it existed in the liquid state; lesion of the cells is thus avoided.

Sublimation consists in eliminating the so-called free water. At a vacuum at about 100 μbar, but which can vary greatly from one product to another, heat is supplied to the product; the ice undergoes sublimation. According to the product and the production requirements, it is possible to vary the temperature during the cycle. The water vapour is captured by a "trap" or "condenser" and the dehydration of the product will proceed continuously. When most of the water has undergone sublimation, the product has lost about 80 to 90% of its water.

Drying consists in removing the captured water from the product. In this step, the vacuum is high, up to about 5 μbar. At this stage, the product is 95% dry.

The amount of microorganism(s) in the composition to be lyophilized may be between $10^1$ cfu/g and $10^{15}$ cfu/g, for example between $10^1$ cfu/g and $10^{12}$ cfu/g.

In the case where the microorganisms or their extracts exist in the form of an aqueous suspension in which the amount of active material may be between 0.1 and 15%, the amount of this suspension in the composition to be lyophilized may be between 1 and 90%.

As specified above, the lyophilizate considered according to the invention may additionally advantageously contain a lyophilization additive, in particular in order to facilitate the lyophilization via texturing of the composition, but also the rehydration of the lyophilizate, when it is in the form of a powder, wafer, tablet, sheet and the like.

By way of example of lyophilization additive, there may be mentioned silica and its derivatives, clays, cellulose derivatives (HEC, HPC, HMPC and the like), polymers of natural origin such as alginates, xanthans, carob gum, guar gums, pectins, agar, carrageenans; polymers of bacterial origin such as hyaluronic acid, dextran, gellan and hydrogels such as carbomers, derivatives of AMPS.

Use may also be made of solid particles and fillers such as:

some talcs, such as "talc Kl" from the company NIPPON or "Talc Extra Steamic OOS" from the company LUZENAC;

some sericites, such as "Sericite BC282" from the company WHITTAKER, hydroxyapatite, microspheres of silica with an open porosity or, preferably, hollow microspheres of silica, such as "SILICA BEADS" from the company MAPRECOS, glass or ceramic microcapsules "MACROLITE" from the company 3M, microporous microspheres of polymers, which have a structure similar to that of a sponge, such as those made of crosslinked acrylate copolymer "Polytrap" by the company DOW CORNING, and those made of polymethyl methacrylate "MICROPEARL M" or "MICROPEARL M 100" by the company SEPPIC, and microcapsules of polymers which contain a single closed cavity and form a reservoir, which may contain a liquid, in particular a cosmetic active agent; they are prepared by known methods such as those described in patents U.S. Pat. No. 3,615,972 and EP-A 0 56219. They may be made, for example, of polymers or copolymers of monomeric acids, amines or esters that are ethylenically unsaturated, of urea-formaldehyde polymers, of polymers or copolymers of vinylidene chloride; by way of example, mention may be made of the microcapsules made of polymers or copolymers of methyl acrylate or methacrylate, or alternatively copolymers of vinylidene chloride and of acrylonitrile; among the latter, there may be mentioned in particular those which contain, by weight, 20-60% of units derived from vinylidene chloride, 20-60% by weight of units derived from acrylonitrile and 0-40% by weight of other units such as units derived from an acrylic and/or a styrene monomer; use may also be made of acrylic polymers or copolymers that are crosslinked, for example in the case of polymers containing a carboxyl group, with diols serving as crosslinking agents; by way of example, mention may be made of the microcapsules made of vinylidene chloride-acrylonitrile copolymer "EXPANCEL" from the company Kemanord Plast, the microcapsules "Q-MAX" from the company Q-MAX and the microcapsules "3 M" from the company.

The amount of lyophilization additives, in the composition to be lyophilized, may vary from 0% to 70% by weight, in particular from 0.1 to 60% by weight, in particular from 0.15 to 50% by weight, for example from 0.2 to 40% by weight, in particular from 0.25 to 30% by weight, relative to the total weight of the said composition.

As for the lyophilizate, it may comprise from 0% to 25% by weight, in particular from 0.5% to 20% by weight, in particular from 1% to 15% by weight, or even from 1.5 to 5% by weight of lyophilization additive(s) relative to the total weight of the said lyophilizate in the dry state.

It may be useful, in a method for lyophilizing a microorganism or microorganisms, to further use at least one cryoprotectant.

Such a compound has the effect of protecting the microorganisms during the freezing step during the vitrification of the water, but also of facilitating future rehydration of the lyophilizate, regardless of the form (wafer, tablet, powder, sheet and the like).

By way of example, there may be mentioned inositol, mannitol, glucose, sucrose, trehalose, maltose, xylitol, polyvinylpyrrolidone, polyvinyl alcohol, dextrin, maltodextrin and in general any monosaccharides and oligosaccharides (2 to 10 units).

Mention may also be made to this effect of starches and modified starches, but also glycols: glycerol, sorbitol, adonitol, propylene glycols, dipropylene glycols, butylene glycol, and amino acids and oligopeptides (2 to 25) such as glutamates, aspartates.

It is also possible to use cysteine, ascorbates, erythorbates and cyclodextrins. They may be used alone or as a mixture.

According to one embodiment of the invention, it is possible to use, as cryoprotectant, a combination of maltodextrin and trehalose.

According to another embodiment, it is possible to use, as cryoprotectant, a combination of maltodextrin and glycerol.

These two types of cryoprotectants are suitable more particularly for the lyophilization of nonphotosynthetic filamentous bacteria and their extracts in the presence of a surfactant with an HLB greater than or equal to 12, and in particular the lyophilization of an extract of *Vitreoscilla filiformis* (ATCC 15551).

The amount of cryoprotectant, in the composition to be lyophilized, may vary from 1 to 80% by weight, for example from 5 to 75% by weight, in particular from 10 to 70% by weight, relative to the total weight of the said composition.

As for the lyophilizate, it may comprise from 5 to 70% by weight, in particular from 10 to 60% by weight, in particular from 20 to 50% by weight of cryoprotectant(s) relative to the total weight of the said lyophilizate in the dry state.

According to one embodiment, the lyophilizate comprises at least one microorganism as defined above, a surfactant with an HLB greater than or equal to 12, a cryoprotectant and a lyophilization additive.

Preferably, the composition to be lyophilized is poured into a shell in order to then form a tablet of the oral lyophilizate type which is then packaged in a blister pack.

The microorganisms, in particular probiotic microorganisms or microorganisms of the nonphotosynthetic filamentous bacterial type, and the surfactant with an HLB greater than or equal to 12, in the form of a lyophilizate, combined or otherwise with other compounds or microorganisms, may be formulated in various galenic forms.

This galenic form may be confined to the lyophilizate of the microorganism and the surfactant with an HLB greater than or equal to 12 as such.

This galenic form may thus consist of a lyophilizate of one or more microorganisms and one or more surfactants with an HLB greater than or equal to 12, including one or more cryoprotectants and/or lyophilizing agents.

However, this galenic form may also include other compounds than those listed above, namely perfumes, flavourings and/or molecules having a biological activity such as vitamins. The choice of these compounds and the adjustment of their quantities are clearly within the competence of a person skilled in the art.

Advantageously, these galenic forms may be free of preservatives or, at the very least, of large quantities of preservatives.

The lyophilizates considered according to the invention may be provided in a dry galenic form, or in the form of suspensions.

According to a preferred variant, the lyophilizates considered according to the invention are provided in a dry galenic form. More particularly, the galenic form may be provided in the form of a powder, of one or more pastilles, of a tablet, of an oral lyophilizate or of a wafer.

These galenic forms may be solubilized and/or dispersed in a physiologically acceptable medium, at the time of, or just before their application, to the keratin material.

Physiologically Acceptable Medium

As specified above, the methods, products and sets according to the invention use a physiologically acceptable medium, that is to say a medium that is nontoxic and capable of being applied to the keratin materials of human beings and that has a pleasant appearance, odour and feel.

According to a first variant, this medium, and in particular the physiologically acceptable medium of step (b) of the method, may be water only.

Accordingly, according to one embodiment, the method according to the invention may consist in solubilizing and/or dispersing the lyophilizate of microorganism(s) and surfactant(s) with an HLB greater than or equal to 12 in water for a bath or a shower or a thermal water and therefore intended to come into contact with a keratin material and in particular the skin.

The bringing of the lyophilizate into contact may be carried out extemporaneously by its direct immersion in water for a bath for example. It is also possible to envisage carrying out this bringing into contact more gradually. Accordingly, devices for shower heads exist designed to allow insertion of solid compositions intended for example for care into the head. The solubilization of the composition is then brought about gradually in contact with the water diffusing through the head.

According to a second variant, the physiologically acceptable medium, in particular the medium of step (b) of the method, is a cosmetic and/or dermatological composition, in other words a composition capable of providing a makeup and/or care at the level of a keratin material such as for example the skin, the lips or the hair. Such a composition is in this case different from pure water.

For example, such a composition may comprise at least one compound chosen from oils, waxes, thickening agents, gelling agents, emulsifying agents, dye substances and/or organic or inorganic fillers.

The cosmetic and/or dermatological compositions considered according to the invention advantageously contain at least one liquid fatty phase.

When the compositions are in anhydrous form, they may be provided in the form of liquids or of soft pastes.

They may also be provided in the form of a lotion, a gel, an O/W, W/O or multiple emulsion.

Advantageously, they may be provided in the form of an emulsion.

The compositions according to the invention may be advantageously provided in the form of an emulsion obtained by dispersing an aqueous phase in a fatty phase (W/O) or of a fatty phase in an aqueous phase (O/W), having a liquid or semiliquid consistency of the milk type, or a soft, semisolid or solid consistency of the cream or gel type, or of a multiple emulsion (W/O/W or O/W/O). These compositions are prepared according to the customary methods.

The emulsions generally contain at least one emulsifier chosen from amphoteric, anionic, cationic or nonionic emulsifiers, which are used alone or as a mixture. The emulsifiers are appropriately chosen according to the emulsion to be obtained (W/O or O/W). The emulsifiers are generally present in the composition in a proportion which may range for example from 0.3 to 30% by weight, and preferably from 0.5 to 20% by weight relative to the total weight of the composition.

For the O/W emulsions, there may be mentioned for example as emulsifiers, nonionic surfactants, and in particular esters of polyols and a fatty acid having a saturated or unsaturated chain comprising for example from 8 to 24 carbon atoms and even better from 12 to 22 carbon atoms, and their oxyalkylenated derivatives, that is to say comprising oxyethylenated and/or oxypropylenated units, such as glyceryl esters of a $C_8$-$C_{24}$ fatty acid, and their oxyalkylenated derivatives; esters of polyethylene glycol and a $C_8$-$C_{24}$ fatty acid, and their oxyalkylenated derivatives; esters of sorbitol and a $C_8$-$C_{24}$ fatty acid, and their oxyalkylenated derivatives; esters of a sugar (sucrose, glucose, alkyl glucose) and a $C_8$-$C_{24}$ fatty acid, and their oxyalkylenated derivatives; fatty alcohol ethers; ethers of a sugar and $C_8$-$C_{24}$ fatty alcohols, and mixtures thereof.

As a glyceryl ester of a fatty acid, there may be mentioned in particular glyceryl stearate (glyceryl mono-, di- and/or tristearate) (CTFA name: glyceryl stearate) or glyceryl ricinoleate, and mixtures thereof.

As an ester of polyethylene glycol and a fatty acid, there may be mentioned in particular polyethylene glycol stearate (polyethylene glycol mono-, di- and/or tristearate), and more especially polyethylene glycol 50 EO monostearate (CTFA name: PEG-50 stearate), polyethylene glycol 100 EO monostearate (CTFA name: PEG-100 stearate) and mixtures thereof.

It is also possible to use mixtures of these surfactants, such as for example the product containing glyceryl stearate and PEG-100 stearate, marketed under the name ARLACEL 165 by the company Uniqema, and the product containing glyceryl stearate (glyceryl mono- or distearate) and potassium stearate, marketed under the name TEGIN by the company Goldschmidt (CTFA name: glyceryl stearate SE).

As an ester of a fatty acid and glucose or alkyl glucose, there may be mentioned in particular glucose palmitate, alkyl glucose sesquistearates such as methyl glucose sesquistearate, alkyl glucose palmitates, such as methyl glucose or ethyl glucose palmitate, fatty esters of methyl glucoside and more especially diester of methyl glucoside and oleic acid (CTFA name: Methyl glucose dioleate); the mixed ester of methyl glucoside and of the oleic acid/hydroxystearic acid mixture (CTFA name: Methyl glucose dioleate/hydroxystearate); ester of methyl glucoside and isostearic acid (CTFA name: Methyl glucose isostearate); ester of methyl glucoside and lauric acid (CTFA name: Methyl glucose laurate); mixture of monoester and diester of methyl glucoside and isostearic acid (CTFA name: Methyl glucose sesquiisostearate); mixture of monoester and diester of methyl glucoside and stearic acid (CTFA name: Methyl glucose sesquistearate) and in particular the product marketed under the name Glucate SS by the company AMERCHOL, and mixtures thereof.

As oxyethylenated ethers of a fatty acid and glucose or alkyl glucose, there may be mentioned for example the oxyethylenated ethers of a fatty acid and methyl glucose, and in particular the polyethylene glycol ether of a diester of methyl glucose and of stearic acid having about 20 moles of ethylene oxide (CTFA name: PEG-20 methyl glucose distearate) such as the product marketed under the name Glucam E-20 distearate by the company AMERCHOL; the polyethylene glycol ether of the mixture of a monoester and diester of methyl glucose and stearic acid having about 20 moles of ethylene oxide (CTFA name: PEG-20 methyl glucose sesquistearate) and in particular the product marketed under the name Glucamate SSE-20 by the company AMERCHOL and that marketed under the name Grillocose PSE-20 by the company GOLDSCHMIDT, and mixtures thereof.

As sucrose esters, there may be mentioned, for example, sucrose palmitostearate, sucrose stearate and sucrose monolaurate.

As fatty alcohol ethers, there may be mentioned, for example, the ethers of polyethylene glycol and of a fatty alcohol comprising from 8 to 30 carbon atoms, and in particular from 10 to 22 carbon atoms, such as the ethers of polyethylene glycol and of cetyl alcohol, stearyl alcohol, cetearyl alcohol (mixture of cetyl and stearyl alcohols). There may be mentioned for example the ethers containing from 1 to 200 and preferably from 2 to 100 oxyethylenated groups, such as those having the CTFA name Ceteareth-20, Ceteareth-30, and mixtures thereof.

As sugar ethers, there may be mentioned in particular alkyl polyglucosides, and for example decyl glucoside such as the product marketed under the name MYDOL 10 by the company Kao Chemicals, the product marketed under the name PLANTAREN 2000 by the company Henkel, and the product marketed under the name ORAMIX NS 10 by the company Seppic; caprylyl/capryl glucoside such as the product marketed under the name ORAMIX CG 110 by the company Seppic or under the name LUTENSOL GD 70 by the company BASF; lauryl glucoside such as the products marketed under the names PLANTAREN 1200 N and PLANTACARE 1200 by the company Henkel; cocoglucoside such as the product marketed under the name PLANTACARE 818/UP by the company Henkel; cetostearyl glucoside optionally in the form of a mixture with cetostearyl alcohol, marketed for example under the name MONTANOV 68 by the company Seppic, under the name TEGOCARE CG90 by the company Goldschmidt and under the name EMULGADE KE3302 by the company Henkel; arachidyl glucoside, for example in the form of a mixture of arachidyl and behenyl alcohols and of arachidyl glucoside marketed under the name MONTANOV 202 by the company Seppic; cocoylethyl glucoside, for example in the form of a mixture (35/65) with cetyl and stearyl alcohols, marketed under the name MONTANOV 82 by the company Seppic and mixtures thereof.

The composition according to the invention may also contain, as emulsifier, an advantageous quantity of amphiphilic polymers.

The expression amphiphilic polymer is understood to mean any polymer comprising both a hydrophilic part and a hydrophobic part and having the property of forming a film separating two liquids of different polarity and thus making it possible to stabilize liquid-liquid dispersions of the direct, inverse or multiple type. The amphiphilic polymers which are more particularly suitable reduce the water/oil interfacial tension up to 10 mN/m, regardless of the oil. These polymers are ionic (anionic or cationic) or amphoteric. They may be water-soluble or water-dispersible. The expression water-soluble is understood to mean the fact that they can disperse in water in the form of a molecular solution. The expression water-dispersible is understood to mean the fact that they can disperse in water in particulate form.

The amphiphilic polymers in accordance with the invention generally have a number-average molecular weight ranging from 1000 to 20 000 000 g/mol, preferably ranging from 20 000 to 8 000 000 and more preferably still from 100 000 to 700 000 g/mol. The quantities of amphiphilic polymers used according to the invention will be chosen from 0.01 to 20%, preferably from 0.1 to 10% and more preferably still from 0.2% to 5% by weight, relative to the total weight of the composition containing it.

It is possible to use more particularly acrylate/$C_{10}$-$C_{30}$-alkyl acrylate copolymers such as the products sold under the names PEMULEN TR1, PEMULEN TR2 and CARBOBOL 1382 by the company GOODRICH, or alternatively mixtures thereof. It is also possible to use acrylate/steareth-20 itaconate copolymers and acrylate/ceteth-20 itaconate copolymers sold under the names STRUCTURE 2001 and STRUCTURE 3001 by the company NATIONAL STARCH. By way of terpolymers which may be used, there may be mentioned the methacrylic acid/methyl acrylate/dimethyl m-isopropenyl benzyl isocyanate of ethoxylated behenyl alcohol terpolymer containing 40 EO, (that is to say containing 40 oxyethylenated groups) sold by the company AMERCHOL under the name VISCOPHOBE DB 1000 NP3-NP4.

It is also possible to mention the crosslinked terpolymers of methacrylic acid, ethyl acrylate, polyethylene glycol (10 EO) ether of stearyl alcohol (Steareth 10), in particular those sold by the company ALLIED COLLOIDS under the name SALCARE SC 80.

The anionic polymers which may be used according to the invention are for example the polymers of isophthalic acid or of sulphoisophthalic acid, and in particular the copolymers of phthlate/sulphoisophthalate/glycol (for example diethylene glycol/phthalate/isophthalate/1,4-cyclohexanedimethanol) sold under the names "Eastman AQ polymer" (AQ35S, AQ38S, AQ55S, AQ48 Ultra) by the company Eastman Chemical.

Mention may also be made of the amphiphilic polymers containing at least one acrylamido-2-methylpropanesulphonic acid (AMPS) unit.

The amphiphilic AMPS polymers according to the invention are chosen in particular from the amphiphilic polymers of at least one acrylamido-methylpropane-sulphonic acid (AMPS) monomer and at least one ethylenically unsaturated comonomer comprising at least one hydrophobic part having from 7 to 30 carbon atoms, in particular from 7 to 22 carbon atoms, or even from 12 to 22 carbon atoms.

The amphiphilic AMPS polymers according to the invention have in general a weight-average molecular weight ranging from 50 000 to 10 000 000 g/mol, in particular from 100 000 to 8 000 000 g/mol and more particularly still from 100 000 to 7 000 000 g/mol.

They may be crosslinked or noncrosslinked.

As a guide, and without this being limiting, there may be mentioned in particular the ethoxylated copolymer of AMPS and $C_{12}$-$C_{14}$ alcohol methacrylate (noncrosslinked copolymer obtained from Genapol LA-070 and AMPS) (CTFA name: Ammonium Acryloyldimethyltaurate/Laureth-7 methacrylate copolymer) marketed under the name ARTISTOFLEX LNC by the company Clariant, the ethoxylated copolymer of AMPS and stearyl methacrylate (25 EO) (copolymer crosslinked with trimethylolpropane triacrylate, obtained from Genapol T-250 and AMPS) (CTFA name: Ammonium Acryloyldimethyltaurate/Steareth-25 Methacrylate Crosspolymer) marketed under the name ARISTOFLEX HMS by the company Clariant, Aristoflex SNC (ethoxylated AMPS/$C_{16}$/$C_{18}$ alcohol methacrylate copolymer (8 moles EP 80/20; CTFA name: Ammonium acryloyldimethyltaurate/steareth-8 mzthacrylate copolymer) and Aristoflex HMB (ethoxylated AMPS/behenyl methacrylate (25 EO), crosslinked with trimethylolpropane triacrylate (TMPTA).

The amphiphilic AMPS polymers according to the invention may be present in amounts of active material ranging from 0.01 to 20% by weight, more preferably from 0.1 to 10% by weight, more preferably still from 0.1 to 5% by weight and more particularly still from 0.3 to 2% by weight relative to the total weight of the composition.

For the W/O emulsions, there may be mentioned for example as emulsifiers dimethicone copolyols such as the mixture of cyclomethicone and dimethicone copolyol, sold under the name "DC 5225 C" by the company Dow Corning, and alkyl dimethicone copolyols such as lauryl methicone copolyol sold under the name "Dow Corning 5200 Formulation Aid" by the company Dow Corning and cetyl dimethicone copolyol sold under the name ABIL EM 90R by the company Goldschmidt, or the polyglyceryl-4 isostearate/cetyl dimethicone copolyol/hexyl laurate mixture sold under the name ABIL WE 09 by the company Goldschmidt. It is also possible to add thereto one or more coemulsifiers. Advantageously, the coemulsifier may be chosen from the group comprising alkylated polyol esters. As alkylated polyol esters, there may be mentioned in particular the esters of glycerol and/or sorbitan and for example polyglycerol isostearate, such as the product marketed under the name Isolan GI 34 and Isolan GPS by the company Goldschmidt, sorbitan isostearate, such as the product marketed under the name Arlacel 987 by the company ICI, sorbitan isostearate and glycerol, such as the product marketed under the name Arlacel 986 by the company ICI, and mixtures thereof.

It is also possible to use, as surfactant for W/O emulsions, a crosslinked elastomeric solid organopolysiloxane comprising at least one oxyalkylenated group, such as those obtained according to the procedure of Examples 3, 4 and 8 of the document U.S. Pat. No. 5,412,004 and of the examples of the document U.S. Pat. No. 5,811,487, in particular the product of Example 3 (example of synthesis) of patent U.S. Pat. No. 5,412,004, such as the one marketed under the references KSG 210, KSG-310, KSG-320, KSG6330, KSG-340 by the company Shin Etsu. It is also possible to use polyglycerolated silicone elastomers, in particular described in Patent Application WO2004/024798, such as those sold under the names "KSG-710", "KSG-810", "KSG-820", "KSG-830", "KSG-840" by the company Shin Etsu.

As emulsifier suitable for obtaining a W/O emulsion, suitable in particular are polyisobutylene surfactants with an esterified succinic end, such as those marketed under the names Lubrizol 5603® and Chemcinnate 2000® by the companies Lubrizol and Chemron.

As examples of oils which can be used in the compositions according to the invention, there may be mentioned:

hydrocarbon oils of animal origin, such as perhydrosqualene;

hydrocarbon oils of plant origin, such as liquid triglycerides of fatty acids comprising from 4 to 10 carbon atoms, such as the triglycerides of heptanoic or octanoic acids or alternatively, for example, sunflower oil, maize oil, soybean oil, gourd oil, grapeseed oil, sesame oil, hazelnut oil, apricot oil, macadamia oil, arara oil, sunflower oil, castor oil, avocado oil, triglycerides of caprylic/capric acids such as those sold by the company Stearineries Dubois or those sold under the names Miglyol 810, 812 and 818 by the company Dynamit Nobel, jojoba oil, shea butter oil;

synthetic esters and ethers, in particular of fatty acids, such as the oils of formulae $R_1COOR_2$ and $R_1OR_2$ in which $R_1$ represents the residue of a fatty acid comprising from 8 to 29 carbon atoms, and $R_2$ represents a branched or unbranched hydrocarbon chain containing from 3 to 30 carbon atoms, such as Purcellin oil, isononyl isononanoate, isopropyl myristate, 2-ethylhexyl palmitate, 2-octyldodecyl stearate, 2-octyldodecyl erucate, isostearyl isostearate; hydroxylated esters such as isostearyl lactate, octyl hydroxystearate, octyldodecyl hydroxystearate, diisostearyl malate, triisocetyl citrate, heptanoates, octanoates, decanoates of fatty alcohols; polyol esters, such as propylene glycol dioctanoate, neopentylglycol diheptanoate and diethylene glycol diisononanoate; and esters of pentaerythritol such as pentaerythrityl tetraisostearate;

linear or branched hydrocarbons of inorganic or synthetic origin, such as volatile or nonvolatile paraffin oils, and their derivatives, isohexadecane, isododecane, petroleum jelly, polydecenes, hydrogenated polyisobutene such as Parleam® oil;

natural or synthetic essential oils such as, for example, eucalyptus oil, lavandin oil, lavender oil, vetiver oil, litsea cubeba oil, lemon oil, sandalwood oil, rosemary oil, camomile oil, savory oil, nutmeg oil, cinnamon oil, hyssop oil, caraway oil, orange oil, geraniol oil, cade oil and bergamot oil;

fatty alcohols having from 8 to 26 carbon atoms, such as cetyl alcohol, stearyl alcohol and a mixture thereof (cetylstearyl alcohol), octyl dodecanol, 2-butyloctanol, 2-hexyldecanol, 2-undecylpentadecanol, oleyl alcohol or linoleyl alcohol;

partially hydrocarbon-based and/or silicone-based fluorinated oils such as those described in the document JP-A-2-295912;

silicone oils such as volatile or nonvolatile polymethylsiloxanes (PDMS) containing a linear or cyclic silicone chain, which are liquid or pasty at room temperature, in particular cyclopolydimethylsiloxanes (cyclomethicones) such as cyclohexasiloxane and cyclopentasiloxane; polydimethylsiloxanes comprising alkyl, alkoxy or phenyl groups, which are pendent or at the silicone chain end, groups having from 2 to 24 carbon atoms; phenylated silicones such as phenyltrimethicones, phenyldimethicones, phenyltrimethylsiloxydiphenylsiloxanes, diphenyldimethicones, diphenylmethyldiphenyl-trisiloxanes, 2-phenylethyl-trimethyl-siloxysilicates, and polymethylphenylsiloxanes; and mixtures thereof.

The expression "hydrocarbon oil" in the list of oils mentioned above, is understood to mean any oil containing predominantly carbon and hydrogen atoms, and optionally ester, ether, fluorinated, carboxylic acid and/or alcohol groups.

The other fatty substances which may be present in the oily phase are for example fatty acids containing from 8 to 30 carbon atoms, such as stearic acid, lauric acid, palmitic acid and oleic acid; waxes such as lanolin, beeswax, carnauba or candelilla wax, paraffin or lignite waxes or microcrystalline waxes, ceresin or ozokerite, synthetic waxes such as polyethylene waxes, Fischer-Tropsch waxes; gums such as silicone gums (dimethiconol).

The compositions according to the invention may comprise a volatile oil.

The expression "volatile oil" is understood to mean, for the purposes of the invention, an oil capable of evaporating in contact with keratin materials within one hour, at room temperature and atmospheric pressure. The volatile organic solvent(s) and the volatiles oils of the invention are organic solvents and volatile cosmetic oils that are liquid at room temperature and have a nonzero vapour pressure, at room temperature and atmospheric pressure, ranging in particular from 0.13 Pa to 40 000 Pa ($10^{-3}$ to 300 mmHg), in particular ranging from 1.3 Pa to 13 000 Pa (0.01 to 100 mmHg), and more particularly ranging from 1.3 Pa to 1300 Pa (0.01 to 10 mmHg).

There may be mentioned, as volatile oils, inter alia, cyclic or linear silicones having from 2 to 6 silicon atoms, such as cyclohexasiloxane, dodecamethylpentasiloxane, decamethyltetrasiloxane, butyltrisiloxane and ethyltrisiloxane. It is also possible to use branched hydrocarbons such as for example isododecane and volatile perfluoroalkanes such as dodecafluoropentane and tetradecafluorohexane, which are sold under the names "PF 5050®" and "PF 5060®" by the company 3M and perfluoromorpholine derivatives, such as 4-trifluoromethylperfluoromorpholine sold under the name "PF 5052®" by the company 3M.

The quantity of oily phase present in the compositions according to the invention may range for example from 0.01 to 50% by weight, and preferably from 0.1 to 30% by weight relative to the total weight of the composition.

The compositions according to the invention may further comprise at least one dye substance chosen for example from pigments, pearlescent agents, dyes, materials with an effect and mixtures thereof.

These dye substances may be present in an amount ranging from 0.01% to 50% by weight, preferably from 0.01% to 30% relative to the total weight of the composition.

The compositions according to the invention may comprise an organic or inorganic filler, in particular in an amount ranging from 0.01% to 50% by weight, relative to the total weight of the composition, preferably ranging from 0.01% to 30% by weight. These fillers may be platelet, spherical or oblong inorganic or organic fillers of any shape, regardless of the crystallographic shape (for example sheet, cubic, hexagonal, orthorhombic or amorphous). There may be mentioned silica, talc, mica, kaolin, lauroyllysine, starch, boron nitride, PTFE powders, PMMA powders, powders of methylsilsesquioxane resin (such as Tospearl 145A from GE Silicone), hollow hemispherical particles of silicone resin (such as NLK 500, NLK 506 and NLK 510 from Takemoto Oil and Fat), barium sulphate, precipitated calcium carbonate, magnesium carbonate and hydrocarbonate, hydroxyapatite, glass or ceramic microcapsules, metal soaps derived from organic carboxylic acids having from 8 to 22 carbon atoms, preferably from 12 to 18 carbon atoms, for example zinc, magnesium or lithium stearate, zinc laurate, magnesium myristate.

The compositions according to the invention may further contain various adjuvants commonly used in the cosmetic field, such as sequestrants; UV screening agents; perfumes; thickeners, and gelling agents.

Among the UV screening agents, there may be mentioned organic and/or inorganic screening agents that are active in UVA and/or UVB, that are hydrophilic and/or lipophilic and/or that are insoluble in the cosmetic solvents commonly used.

Depending on the fluidity of the composition which it is desired to obtain, it is possible to incorporate into the composition one or more gelling agents, in particular which are hydrophilic, that is to say soluble or dispersible in water.

As hydrophilic gelling agents, there may be mentioned in particular water-soluble or water-dispersible thickening polymers. These may be chosen in particular from: modified or unmodified carboxyvinyl polymers such as the products marketed under the names Carbopol (CTFA name: carbomer) and Pemulen (CTFA name: Acrylates/C10-30 alkyl acrylate crosspolymer) by the company Goodrich; polyacrylates and polymethacrylates such as the products sold under the names Lubrajel and Norgel by the company GUARDIAN or under the name Hispagel by the company HISPANO CHIMICA; polyacrylamides; polymers and copolymers of 2-acrylamido-2-methylpropane-sulphonic acid, which are optionally crosslinked and/or neutralized, such as the poly (2-acrylamido-2-methylpropanesulphonic acid) marketed by the company CLARIANT under the name "Hostacerin AMPS" (CTFA name: ammonium polyacryldimethyltauramide); crosslinked anionic copolymers of acrylamide and AMPS, which exist in the form of a W/O emulsion, such as those marketed under the name SEPIGEL 305 (C.T.F.A. name: Polyacrylamide/C13-14 Isoparaffin/Laureth-7) and under the name SIMULGEL 600 (C.T.F.A. name: Acrylamide/Sodium acryloyldimethyltaurate copolymer/Isohexadecane/Polysorbate 80) by the company SEPPIC; polysaccharide biopolymers such as xanthan gum, guar gum, carob gum, acacia gum, scleroglucans, chitin and chitosan derivatives, carrageenans, gellans, alginates, celluloses such as microcrystalline cellulose, carboxymethylcellulose, hydroxymethylcellullose and hydroxypropylcellulose, and mixtures thereof.

As lipophilic gelling agents, there may be mentioned for example modified clays such as modified magnesium silicate (bentone gel VS38 from RHEOX), hectorite modified with distearyldimethylammonium chloride (CTFA name: Disteardimonium hectorite) marketed under the name "bentone 38 CE" by the company RHEOX.

A composition of the invention may be provided in any of the galenic forms which may be envisaged.

In particular, a composition according to the invention may be in the form of an aqueous, alcoholic or aqueous-alcoholic solution, a dispersion of the lotion or serum type; a water-in-oil, oil-in-water or multiple emulsion; a suspension; microcapsules or microparticles; vesicular dispersions of the ionic and/or nonionic type; an aqueous or oily lotion or in the form of a serum, an aerosol composition also comprising a propellant under pressure.

A composition according to the invention may be provided in the form of a hair care composition, in particular a shampoo, a treatment lotion, a hair styling cream or gel, restructuring lotions for the hair, an anti-hair-loss lotion or gel, an antiparasitic shampoo.

It may also be provided in the form of a cleansing, protective, treatment or care composition for the face, for the hands, for the feet, for the large anatomical folds or for the body (for example day creams, night cream, makeup-removing cream, anti-sun composition, protective or care body milks, after-sun milks, care lotion, gel or foam for the skin, as cleansing lotions); a makeup composition for the body or the face such as a foundation; a bath composition; a deodorant composition; an aftershave composition; a composition against insect bites; an anti-pain composition; a composition for treating certain skin diseases such as eczema, rosacea, psoriasis, lichens, severe pruritus.

When a composition according to the invention is intended for a peeling-type use, it may also be provided in any of the galenic forms mentioned above as long as it can be easily removed by rinsing, and in particular in the form of an aqueous gel, or an aqueous or aqueous-alcoholic solution.

The mixture of the lyophilized form and of the physiologically acceptable medium or of the two respective compositions according to the invention may be applied by any means allowing uniform distribution and in particular with the aid of cotton wool, a stick, a brush, a gauze, a spatula or a pad, or alternatively by spraying, and may be removed by rinsing with water or with the aid of a mild detergent.

A composition according to the invention may further comprise one or more additional cosmetic or therapeutic active agents, such as for example anti-UV agents, antiageing/anti-wrinkle agents (such as anti-glycation agents, agents stimulating the synthesis of dermal or epidermal macromolecules and/or preventing their degradation, stimulating the proliferation of the fibroblasts and/or the keratinocytes or stimulating the differentiation of the keratinocytes, muscle relaxants), moisturizing agents, desquamating agents, anti-pollution and anti-free-radical agents, slimming agents, agents acting on the microcirculation, agents acting on the energy metabolism of the cells, tightening agents, depigmenting or propigmenting agents, desquamating agents, anti-acne agents or alternatively anti-inflammatory/anti-irritant agents.

Mention may also be made of all the active agents known for their activity on skin ageing such as the keratolytic or prodesquamating agents, for example α-hydroxy acids, β-hydroxy acids, α-ceto acids, retinoids and esters thereof, retinol, retinoic acid and its derivatives; vitamins C, B3 or PP, B5, E and the derivatives of these vitamins and in particular their esters, vitamin K and its derivatives (K1, K2, and the like); anti-free-radical agents; DHEA and its derivatives; coenzyme Q10; bleaching and depigmenting agents such as kojic acid, para-aminophenol derivatives, arbutin and derivatives thereof, and mixtures thereof.

It can be understood, in the light of the various variant embodiments discussed above, why bringing the lyophilizate into contact with the physiologically acceptable medium is not necessarily carried out at room temperature.

Accordingly, in the case where the physiologically acceptable medium is represented by water, for example for a bath or for a shower, the temperature may be greater than room temperature and may reach a temperature close to body temperature, that is to say 37° C., or even higher.

On the other hand, in the case where the physiologically acceptable medium is represented by a cosmetic and/or dermatological composition, the temperature for bringing the lyophilizate into contact with the said physiologically acceptable medium is generally room temperature.

In this second variant, the lyophilizate is generally introduced into the packaging device containing the composition. However, it is also possible to envisage that the user only removes a portion of this composition and carries out the extemporaneous mixing with the whole or a portion of the lyophilizate, for example in the hollow of the hand, directly at the site of application or alternatively in or at the surface of an auxiliary support.

The invention also relates to a cosmetic or dermatological care product combining with at least one lyophilizate in accordance with the invention a cosmetic or dermatological composition different from the lyophilizate and in particular different from water. In other words, the cosmetic composition is advantageously not solely formed of pure water.

This composition is in particular capable of solubilizing or dispersing the lyophilizate.

This composition generally comprises a physiologically acceptable medium, in particular as defined above.

The lyophilizate will be used in the form of a mixture with this composition prepared extemporaneously by the user.

The product according to the invention may be designed for a single use, in which case the whole of the first composition based on the lyophilizate is mixed with the associated composition and the whole of the mixture is applied to the site to be treated.

It is also possible to envisage that the lyophilizate forming the first composition is provided in a galenic form suitable for the removal of only a portion thereof. For example, this may be tablets or oral lyophilizates. According to this variant embodiment, the user uses for example only a tablet or an oral lyophilizate which they mix with a sufficient quantity of the second composition to allow the solubilization or dispersion of the said lyophilizate therein.

Advantageously, the first and second compositions may be combined in a single packaging allowing them to be preserved separately one from the other.

As specified above, the invention also relates to a packaging set.

More particularly, this set comprises at least:
i. a first compartment containing at least one lyophilizate containing at least one live or inactivated physiologically acceptable microorganism, one of its metabolites or one of its fractions and at least one surfactant with an HLB greater than or equal to 12,
ii. a second compartment containing a physiologically acceptable medium separate from the said lyophilizate, the said second compartment being, prior to the use of the set, isolated in a leakproof manner from the first compartment, and
iii. means for, in response to actuation, allowing communication to be established between the first and second compartments, and the said lyophilizate to be brought into contact with the said physiologically acceptable medium.

Such a set advantageously allows its two components, packaged separately in respectively the first and second compartments forming the said set, to be brought into contact extemporaneously.

These compartments may be made, for example, using a sheet, for example a sheet of a flexible thermoplastic material, folded over itself and whose edges are sealed together so as to respectively delimit each of the two compartments.

This material may be a sheet made of an aluminium material or of a thermoplastic material such as polyolefin materials such as polyethylene (PE) or polypropylene (PP), or alternatively of polyethylene terephthalate (PET), ethylene vinyl hydroxide (EVOH), ethylene vinyl acetate (EVA), polyvinyl chloride (PVC) or of polyamide (PA). This set is also provided with means allowing communication to be established between the first and second compartments and therefore between their respective contents.

Advantageously, the said physiologically acceptable medium of the second compartment is fluid, and preferably liquid, thus pressure exerted on the walls of the second compartment makes it possible to easily generate a flow of the composition forming the said medium.

For example, the lyophilized form and more particularly the composition which it forms is provided in a dry galenic form, for example a powder intended to become solubilized or dispersed in contact with the physiologically acceptable medium.

The set is also advantageously provided with a means suitable for the distribution of the lyophilizate and of the physiologically acceptable medium.

Such a set is in particular described in the document FR 2 876 356.

The invention will be understood more clearly on reading the description which follows and on examining the figures accompanying it. These are presented only as a guide and do not at all limit the invention. The figures show:

FIG. 1: a perspective view of a set according to the invention;

FIG. 2: a cross sectional view of the set of FIG. 1 along a sectional plane indicated A-A;

FIG. 3: a cross sectional view of the set of FIG. 1 along a sectional plane indicated B-B;

FIG. 1 shows a set according to the invention. Set 1 comprises a first compartment 2 and a second compartment 3 juxtaposed over each other. A portion of the peripheral edge 4 of the first compartment 2 is adjacent to a portion of the peripheral edge 5 of the second compartment 3, together they form a common border 6 on either side of which the compartments are respectively defined.

FIGS. 1 to 3, the two compartments 2 and 3 are presented in the form of sachets, for example joined in the form of a string of beads.

The first compartment 2 forms in particular a sachet delimited by a top wall 7 and a bottom wall 8 joined to each other by a link 9 formed at the level of their respective peripheral edges 4a and 4b. The first compartment 2 is configured to contain a first composition 10.

The second compartment 3 is preferably linked in an identical way to the first compartment. It comprises a top wall 11 and a bottom wall 12 joined to each other by a link 13 formed at the level of their respective peripheral edges 5a and 5b. The second compartment 3 is configured to contain a second composition 14.

At least one of the walls 11 or 12 of the second compartment 3 is made of a deformable material, it being possible for the other of the walls of the second compartment 3 to which it is linked to be made of a rigid plate. Likewise, the first compartment 2 may comprise one of its rigid walls, for example configured to form a convex shell.

To allow, at the appropriate time at least a flow of the physiologically acceptable medium to the first compartment 2, the set 1 according to the invention comprises a channel 15 extending across the common border 6.

The channel 16, provided with two ends 23 and 24, is for example blocked by a hermetic blocking linkage 21 formed at the level of an internal periphery of this channel 16. The blocking linkage 21 is preferably weak and easy to break. It may be chosen in particular so as to break under the effect of an extremely high pressure exerted in the second compartment 3. This extremely high pressure is for example obtained by exerting for example a manual pressure on the external periphery of the at least one deformable wall of the second compartment.

As a variant, the second compartment 3 may be provided with a third opening sealed with an adhesive tape.

The user removes this adhesive tape in order to collect its content, placed in contact. Such an opening is particularly advantageous when the physiologically acceptable medium contained in the second compartment is used in a form impregnated in a substrate for application. In this case, the substrate for application 10 may be made of a material of natural or synthetic origin, which is preferably nonwoven, but which may also be a foam or a woven material.

Such impregnated substrates, or wipes, may be wet or dry. The wet substrates may be impregnated with an aqueous composition such as a makeup-removing lotion, a makeup-removing milk or a care product for example, and they are, after bringing into contact with the lyophilizate, directly applied to the face, the body or the hair. They may also be impregnated with an anhydrous composition containing for example a mixture of oils and surfactants, and the substrate is then, after bringing into contact with the lyophilizate, either directly used on the face or the body, or moistened beforehand with some water in order to emulsify the oil/surfactant mixture before application to the body, the face or the hair.

A set or a product according to the invention may be intended for a care and/or makeup and/or dermatological cosmetic application.

The examples given below are presented by way of illustration and do not limit the field of the invention.

EXAMPLES

Example No. 1

Preparation of a Lyophilized Composition

| Composition of the formula before lyophilization | |
|---|---|
| Suspension of *Vitreoscilla filiformis* (ATCC15551) as described in WO 94/02158 inactivated, ontaining 5% active material | 85.75% |
| Mannitol | 10% |
| Decyl glucoside (marketed by the company HENKEL under the name "Plantacare 2000 UP ®") (corresponding to 2% active material) | 4% |
| Xanthan | 0.25% |

The composition to be lyophilized is poured into a multivesicular shell (blister type for tablets) in an amount of 2 g per vesicle. The set is placed in a lyophilizer and persons skilled in the art set the lyophilization parameters (freezing temperature (about −40° C.), sublimation temperature (about −20° C.), secondary drying temperature (about 20° C.), partial vacuum (about 400 μbar)).

An oral lyophilizate type tablet is obtained having a geometry determined by that of the cavity, whose weight is about 0.90 g. The cavities are then covered with heat-sealed aluminium foil.

After lyophilization, the final composition is of the order:

| | |
|---|---|
| *Vitreoscilla filiformis* (ATCC15551) | 25.9% |
| Mannitol | 60.7% |
| Decyl glucoside (marketed by the company HENKEL under the name "Plantacare 2000 UP ®") | 12.0% |
| Xanthan | 1.5% |

A lyophilizate is obtained which disperses perfectly and spontaneously in contact with water or with a cosmetic composition comprising an aqueous phase, in particular a cosmetic composition with a continuous aqueous phase.

Example No. 2

Preparation of a Lyophilized Composition

| Composition of the formula before lyophilization | |
|---|---|
| Suspension of *Vitreoscilla filiformis* (ATCC15551) as described in WO 94/02158 inactivated, containing 5% active material | 42.9% |
| Mannitol | 10% |
| Polysorbate 20, marketed by the company UNIQEMA under the name "Tween 20" | 2% |
| Xanthan | 0.25% |
| Distilled water | qs 100% |

This preparation is treated according to the protocol described in Example 1.

After lyophilization, the final composition is of the order:

| | |
|---|---|
| *Vitreoscilla filiformis* (ATCC15551) | 14.82% |
| Mannitol | 69.54% |
| Polysorbate 20, marketed by the company UNIQEMA under the name "Tween 20" | 13.9% |
| Xanthan | 1.74% |

A lyophilizate is obtained which disperses perfectly and spontaneously in contact with water or with a cosmetic composition comprising an aqueous phase, in particular a cosmetic composition with a continuous aqueous phase.

Example No. 3

Lyophilized Composition

| | |
|---|---|
| *Lactobacillus acidophilus* | 1 × 10$^6$ cfu |
| *Lactobacillus paracasei* | 1 × 10$^6$ cfu |
| Maltodextrin | 25% |
| Mannitol | 65% |
| Polysorbate 20, marketed by the company UNIQEMA under the name "Tween 20" | 5% |
| Trehalose | qs 100% |

Example No. 4

Antiageing Day Cream for the Face

Phase A1:

| | |
|---|---|
| Diglyceryl distearate marketed by the company Nihon Emulsion under the reference "EMALEX PSGA" | 1.75% |
| Polyoxyethylenated methyl glucose distearate 20 EO marketed by the company Amerchol under the name "GLUCAM E 20 DISTEARATE" | 1.15% |
| Sodium dicetyl phosphate | 0.75% |
| Stearyl heptanoate | 4.00% |
| Petroleum jelly | 1.5% |
| Avocado oil | 3.2% |
| Jojoba oil | 3.0% |
| Volatile silicone oil | 2.7% |
| Vitamin E acetate | 1.0% |
| Natural D-α-tocopherol marketed by the company Henkel under the name "COPHEROL 1300" | 1.0% |
| Vitamin F glycerides | 3.0% |
| Retinol palmitate marketed by the company Fluka, containing a dose of 1500 IU/mg | 0.5% |

Phase A2:

| | |
|---|---|
| Silicone gum marketed by Dow Corning under the name "Q2 - 1403 FLUID" | 3.00% |
| Perfume | 0.30% |

Phase B:

| | |
|---|---|
| Glycerine | 3.00% |
| Hydroxyproline | 1.00% |
| D-panthenol | 1.00% |
| Methylparaben | 0.20% |
| Demineralized water | qsp 100.00% |

Phase C:

| | |
|---|---|
| Mixture of carboxyvinyl polymers marketed under the name "CARBOPOL 940" by the company Goodrich | 0.40% |
| Demineralized water | 9.50% |
| Triethanolamine | 0.25% |

The oily phase A1 and the aqueous phase B are heated separately to a temperature of 80° C.

While stirring at 4000 rpm provided by the Moritz type homogenizer Turbo Lab 2100, phase B is poured over phase A1 and these stirring and temperature conditions are maintained for 30 minutes.

The mixture is then introduced into an OBL type Soavi high-pressure homogenizer regulated at the pressure of 500 bar for 3 consecutive passages.

A stabilized oil-in-water emulsion is thus obtained whose oil globules have a mean size of less than 200 nm and a polydispersity value of less than 0.1, as measured by a laser granulometer of the AMTECH BI 90 type.

The emulsion is then cooled in order to bring it to room temperature, which takes about 60 minutes. The oily phase A2 is then added to the emulsion and the whole is subjected to stirring provided by Trbo Lab 2100 at the speed of 3000 rpm for 10 min, after which this premixture is introduced into the Soavi-OBL regulated at the pressure of 350 bar for 2 additional passages.

After each of these two passages, the product is cooled to room temperature.

The phase C is added to this emulsion A1+B+A2, and the whole is stirred with the aid of a Rayneri homogenizer equipped with a deflocculating type turbine at the speed of 2500 rpm for 30 min at room temperature.

At the time of application, the consumer solubilizes an oral lyophilizate of Example 1, 2 or 3 in a blob of antiageing care product of Example 4 placed in the hollow of their hand, and thus obtains an antiageing care product containing live probiotics.

The invention claimed is:

1. A lyophilizate obtained by lyophilization of a composition, the composition comprising:
   at least one live or inactivated physiologically acceptable microorganism, one of its metabolites, an extract thereof, or one of its fractions, at least one surfactant with an HLB greater than or equal to 12, and at least one lyophilization additive selected from the group consisting of polymers of natural origin,
   wherein the microorganism is selected from the group consisting of *Lactobacillus johnsonii, Lactobacillus reuteri, Lactobacillus rhamnosus, Lactobacillus paracasei, Lactobacillus casei, Bifidobacterium bifidum, Bifidobacterium breve, Bifidobacterium longum, Bifidobacterium animalis, Bifidobacterium lactis, Bifidobacterium infantis, Bifidobacterium adolescentis, Bifidobacterium pseudocatenulatum*, nonphotosynthetic filamentous bacteria, and mixtures thereof, and
   wherein the lyophilizate is in dry form,
   wherein the lyophilizate comprises a lyophilizate-redissolution effective amount of from 5 to 14% by weight of surfactant(s) with an HLB greater than or equal to 12, relative to the total weight of the said lyophilizate in the dry form,
   wherein the surfactant(s) with an HLB greater than or equal to 12 is selected from the group consisting of alkyl and polyalkyl esters of poly(ethylene oxide), alkyl and polyalkyl esters of sorbitan, optionally polyoxyethylenated, alkyl and polyalkyl glucosides and polyglucosides, alkyl and polyalkyl esters of glycerol, optionally polyoxyethylenated, alkyl ether sulphates, sarcosinates, betaines and mixtures thereof;
   wherein the microorganism, metabolite, extract and/or fraction thereof is formulated in a quantity equivalent from 0.1% to 50% of active material or dry matter, of the lyophilized formula or support containing the microorganism, metabolite, extract and/or fraction thereof;
   wherein the lyophilization additive is present in an amount of from 0.5% to 5% by weight relative to the total weight of said lyophilizate, and
   wherein the lyophilizate comprises at least one cryoprotectant.

2. A method for the cosmetic treatment of a keratin material comprising:
   bringing a cosmetic composition comprising a physiologically acceptable medium and the lyophilizate according to claim 1 into contact with the keratin material.

3. The lyophilizate according to claim 1, wherein the microorganism is at least one nonphotosynthetic filamentous bacterium or one of its extracts, selected from the group consisting of *Vitreoscilla filiformis* (ATCC 15551), *Vitreoscilla beggiatoïdes* (ATCC 43181), *Beggiatoa alba* (ATCC 33555), *Flexithrix dorotheae* (ATCC 23163), *Leucothrix mucor* (ATCC 25107), and *Sphaerotilus natans* (ATCC 13338).

4. The lyophilizate according to claim 1, wherein the lyophilizate contains from 101 cfu/g to 1015 cfu/g of microorganisms.

5. The method according to claim 1, wherein the physiologically acceptable medium consists of water.

6. An extemporaneous cosmetic or dermatological care product for a keratin material comprising at least:
   a first composition completely ear partially formed of a lyophilizate according to claim 1, and
   a second composition containing a physiologically acceptable medium separate from the first composition, wherein the physiologically acceptable medium is in liquid form and is capable of solubilizing or dispersing the lyophilizate in the first composition.

7. A packaging set comprising at least:
   a first compartment containing at least one lyophilizate according to claim 1,
   a second compartment containing a physiologically acceptable medium separate from the lyophilizate, the second compartment being, prior to the use of the set, isolated in a leakproof manner from the first compartment, wherein the physiologically acceptable medium is in liquid form, and
   wherein, in response to actuation, communication is established between the first and second compartments, and the lyophilizate is brought into contact with the physiologically acceptable medium.

8. The lyophilizate according to claim 1, wherein the microorganism is an extract of *Vitreoscilla filiformis* (ATCC 15551).

9. The lyophilizate according to claim 1, wherein the fractions and/or metabolites of the microorganisms are formulated in a quantity equivalent from 1% to 40% of active material or dry matter, of the lyophilized formula or support containing the fractions and/or metabolites.

10. The lyophilizate according to claim 1, wherein the polymer of natural origin is xanthan.

11. The lyophilizate according to claim 1, wherein the lyophilization additive is present in an amount of from 1.5% to 5% by weight relative to the total weight of said lyophilizate.

* * * * *